United States Patent
Robbs et al.

(10) Patent No.: US 6,790,469 B2
(45) Date of Patent: Sep. 14, 2004

(54) METHOD AND APPARATUS FOR TREATING TUBERS WITH A POWDERED ORGANIC COMPOUND

(75) Inventors: Steven E. Robbs, Meridian, ID (US); Michael B. Machurek, Meridian, ID (US)

(73) Assignee: Industrial Ventilation, Inc., Nampa, ID (US)

( * ) Notice: Subject to any disclaimer, the term of this patent is extended or adjusted under 35 U.S.C. 154(b) by 315 days.

(21) Appl. No.: 09/977,519

(22) Filed: Oct. 12, 2001

(65) Prior Publication Data

US 2003/0072855 A1 Apr. 17, 2003

(51) Int. Cl.[7] .................. A23L 1/212; A23L 3/3134; A23L 3/3454
(52) U.S. Cl. .................. 426/335; 426/615; 426/637
(58) Field of Search ............... 426/615, 637, 426/335

(56) References Cited

U.S. PATENT DOCUMENTS

| | | |
|---|---|---|
| 4,226,179 A | 10/1980 | Sheldon et al. |
| 5,723,184 A | 3/1998 | Yamamoto |
| 5,935,660 A | 8/1999 | Forsythe et al. |
| 6,432,882 B1 * | 8/2002 | Yamamoto .................. 504/304 |
| 2002/0136839 A1 * | 9/2002 | Forsythe et al. ............ 427/421 |

* cited by examiner

Primary Examiner—Helen Pratt
(74) Attorney, Agent, or Firm—Angus C. Fox, III

(57) ABSTRACT

The present invention provides both a process and apparatus for treating tubers in storage with chlorpropham (CIPC) dust or the dust of any other similar organic compound. The process includes the steps of forming minute particles of solid CIPC particles from a larger block or chunks of solid CIPC, and inducting the particles into an airstream which transports the particles to a tuber storage shed. For a preferred embodiment of the invention, the blocks or chunks of solid CIPC are fed into a hammer mill or like apparatus, which pulverizes the solid CIPC. Insufficiently fine particles are returned to the mill for further pulverization. Fine powder consisting of particles, each of which has a major dimension of less than about 5 micrometers, is transported by the ducted airstream from the separator to a storage shed containing a pile of tubers. The powder filters through the pile and coats exposed surfaces of the exposed tubers.

12 Claims, 3 Drawing Sheets

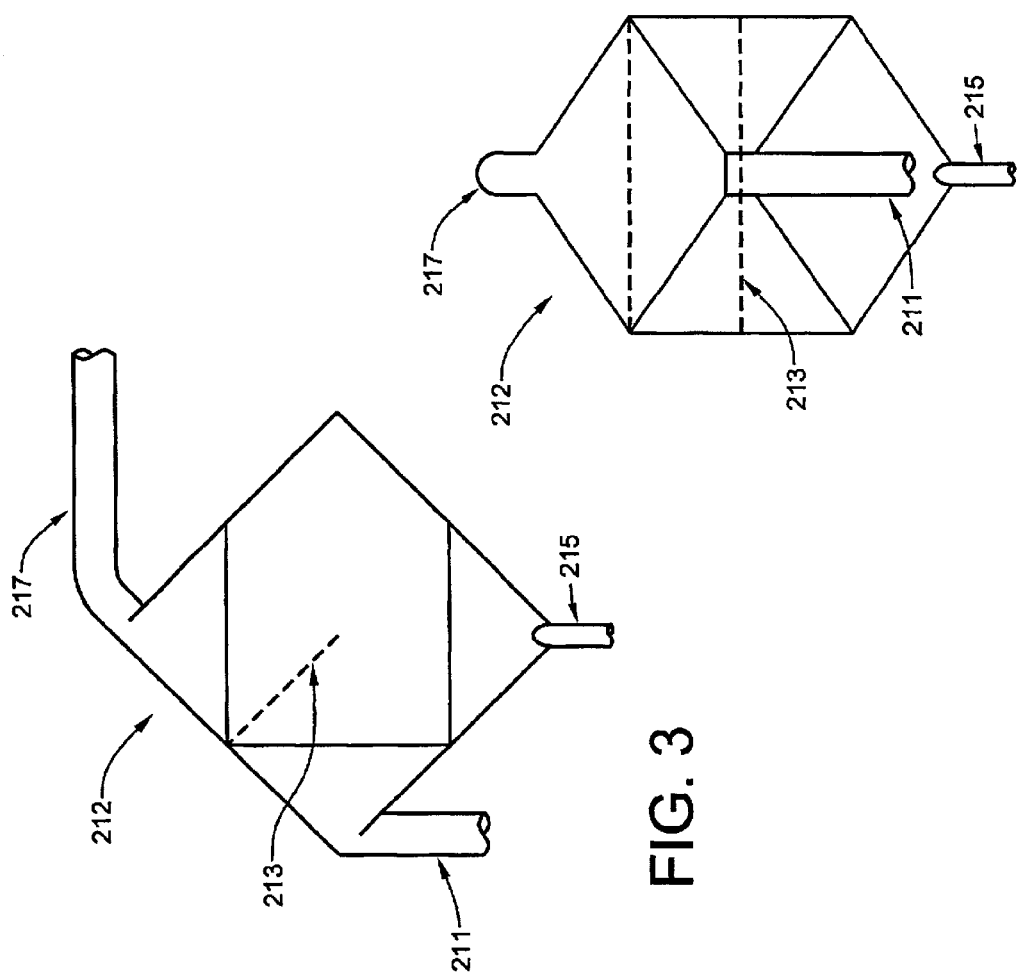

METHOD AND APPARATUS FOR TREATING TUBERS WITH A POWDERED ORGANIC COMPOUND

BACKGROUND OF THE INVENTION

1. Field of the Invention

This invention relates to a method and apparatus for making organic compound particles and, subsequently, atomizing those particles. The invention is disclosed in the context of a method and apparatus for atomizing chlorpropham, a compound widely used in the agricultural industry to inhibit sprouting of stored tubers.

2. Description of Related Art

Figure 2:
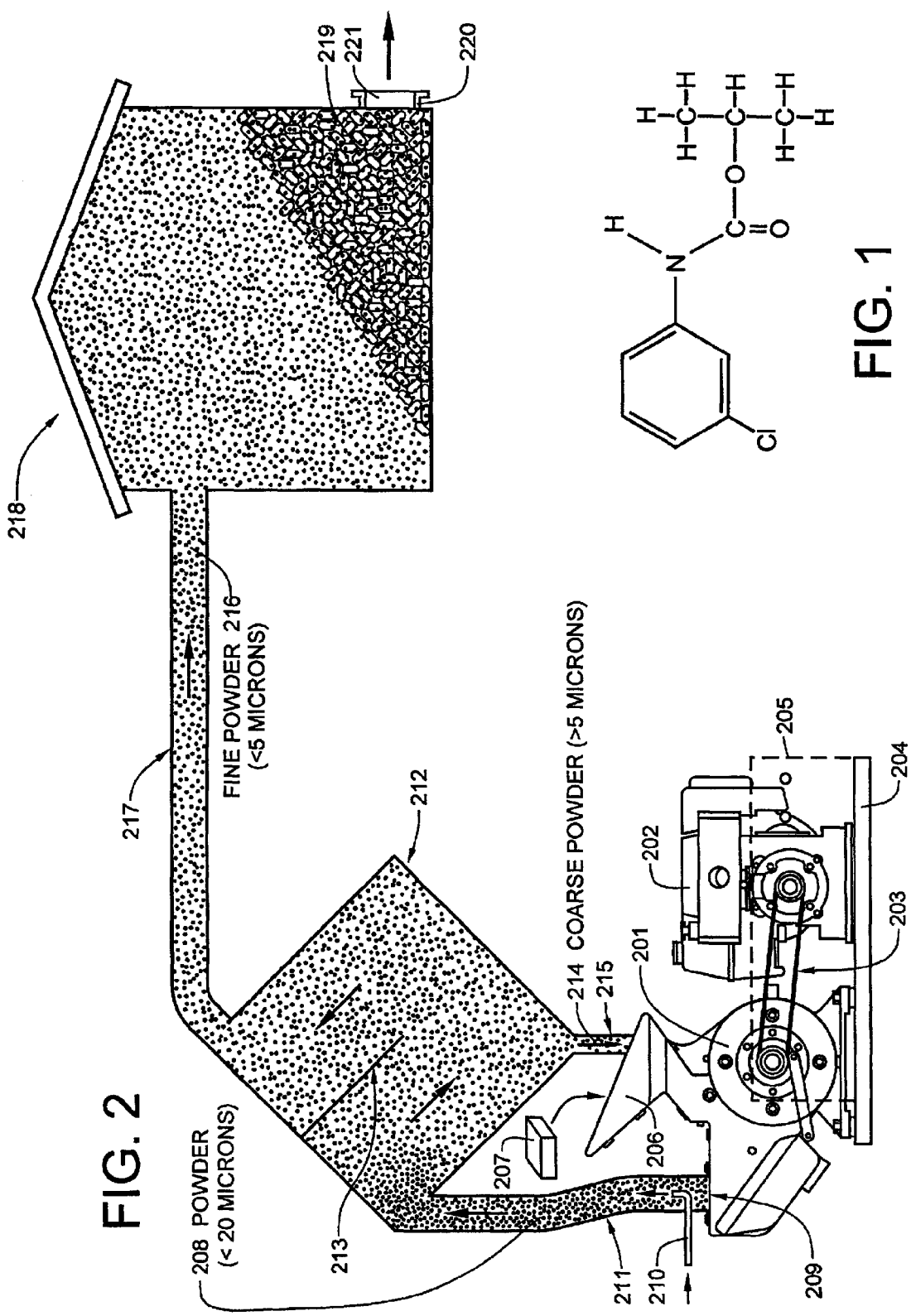
Figure 1:
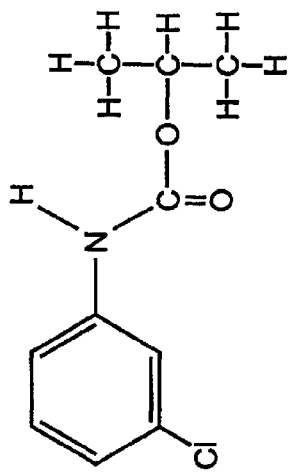
Figure 6:
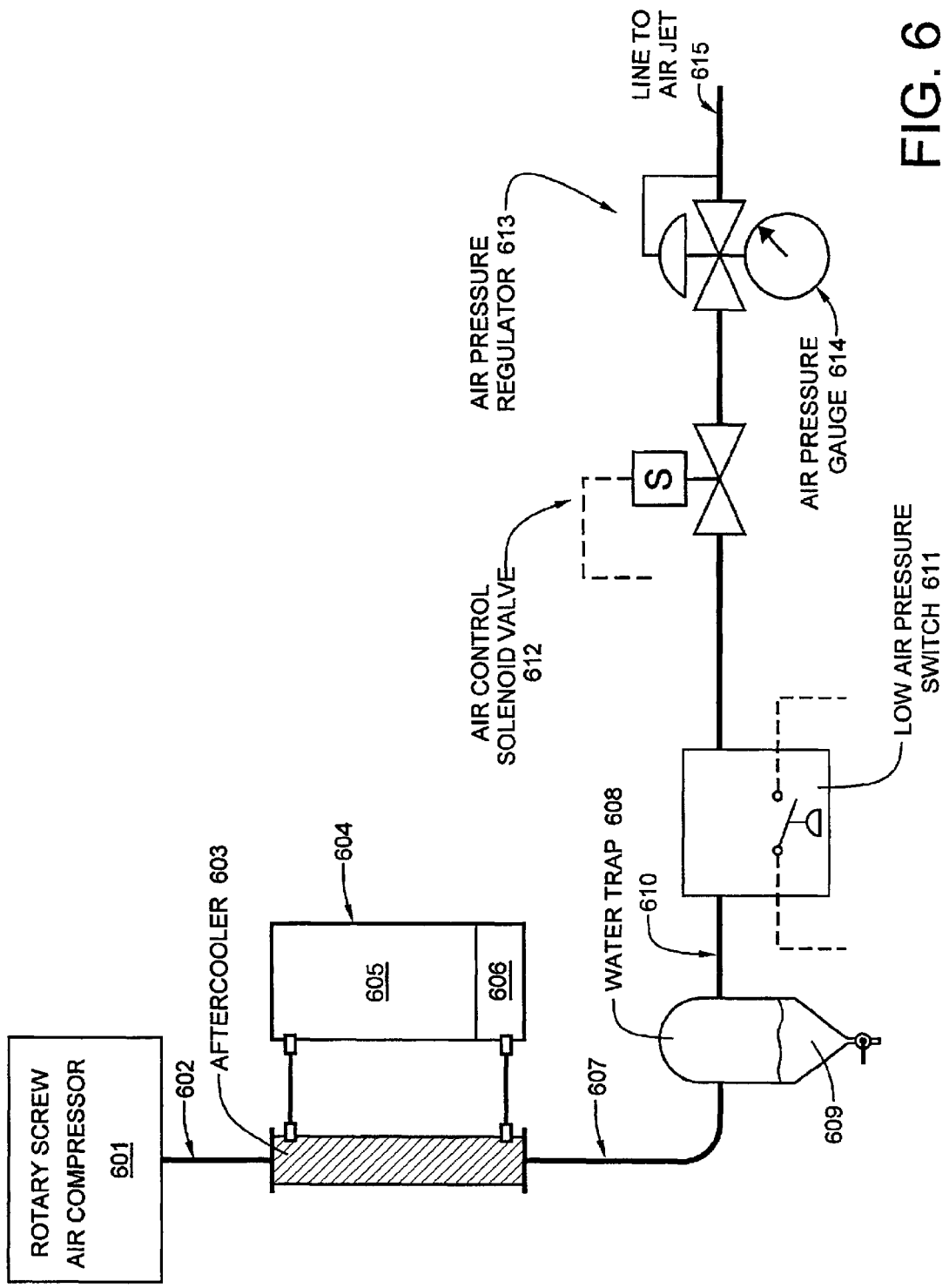

It is often desirable to store certain agricultural produce until a sale under favorable economic terms can be consummated and the produce delivered to the purchaser. During storage, it is essential that freshness of the produce be maintained. Tubers, such as potatoes, are frequently stored as bulk piles in quantities of 2,270,000 to over 22,700,000 kilograms (5,000,000 to over 50,000,000 U.S. lbs.) in dark, underground storage cellars where the temperature is maintained within a range of about 4.5° C. to 12.8° C. (approximately 40 to 55° F.). Untreated tubers will generally sprout over time, even in the absence of light. If the sprouting is allowed to continue unchecked, the tubers become commercially worthless. Isopropyl-3-chlorocarbonilate, an organic compound commonly known as CIPC or chlorpropham and marketed under a variety of trade names, is currently the only registered post-harvest sprout inhibitor used in potato storages in the United States. Used also as an herbicide, Its use as a potato sprout inhibitor was first reported by P. C. Marth in 1952, and its use for that purpose was later patented by the Pittsburgh Plate & Glass Co. The molecular structure of CIPC is depicted in FIG. 1. CIPC has a molecular weight of 213.66, a melting point of about 41° C., a vaporization temperature of about 246° C., and a vapor flash point of about 427° C.

CIPC inhibits potato sprout development by interfering with spindle formation during cell division. Cell division is extremely important during the wound healing or curing period after potatoes are placed into storage. Wound healing requires the production of two to five new cell layers formed by cell division. If CIPC is applied to the potatoes before the wound healing process is complete, excessive losses due to tuber dehydration and disease can occur. CIPC may be applied any time after the wound healing process is complete but before the tubers break dormancy in early spring. It is not recommended to store In order to suppress the sprouting of a tuber, the tuber must be covered with a thin film of chloroprofam. CIPC is applied to the tubers as an aerosol or as an emulsifiable concentrate. The emulsifiable concentrate is generally applied to the potatoes as a direct spray during the fresh packing operation. CIPC aerosols are generally applied to potatoes in bulk storage.

Several methods have been developed for applying CIPC aerosols to potatoes in bulk storage. U.S. Pat. No. 4,226,179 to Sheldon, III et al. discloses a process whereby CIPC, either without solvent or with a relatively small amount of solvent, is atomized at a temperature of less than 121° C. The aerosol is formed in a fogger having a cylindrical mist chamber in which ultrasonic resonance nozzles atomize the chemical agent. A tangentially introduced air flow and a helical baffle plate in the mist chamber cause centrifugal separation, leaving smaller particles near the center of the mist chamber. These small particles are carried by an airflow duct to a storage chamber containing potatoes. The aerosol condenses on the potatoes, thereby forming a growth inhibiting film thereon. U.S. Pat. No. 5,723,184 to Yamamoto discloses a process whereby CIPC is heated to a molten state, pressurized, further heated and introduced into a heated airstream that is ducted to a storage chamber containing potatoes. U.S. Pat. No. 5,935,660 to Forsythe, et al. discloses a process similar to that of Yamamoto whereby solid CIPC is melted and then converted to an aerosol either by a pressurized hot air stream or by a combustion gas stream.

There are several drawbacks to the aerosol formation processes which inject molten CIPC into a heated airstream. The first is that of CIPC solidifying within the transport or injector lines. If an aerosol generation system having molten CIPC within the transport or injector lines is allowed to cool, the CIPC will solidify, making further operation of the equipment impossible until the CIPC returns to its molten state. In order to effectively deal with this operational quirk, molten CIPC must be removed from the transport lines when the equipment is shut down. This is typically done by replacing the molten CIPC with a solvent. Nozzle clogging can also be a problem with this type of equipment. If movement of the heated liquid CIPC is relied on to maintain the temperature of fluid transport lines removed from a primary heat source, nozzle clogging will result in solidification of CIPC within the transport lines within a short time. For this reason, liquid transport lines must also be heated.

A second drawback related to the use of melted CIPC is the risk of scalding and burns to equipment operators, whether it be from the leakage of the scaldingly hot liquid CIPC from the liquid transport lines, or the need to repair application equipment containing melted CIPC. Though the maintenance risk may be minimized by allowing the equipment is to cool to safer, lower temperatures, the CIPC in the liquid transport lines will solidify at those safer temperatures, thereby hampering efforts to restart the aerosol generation process.

A third drawback to the use of melted CIPC for the generation of aerosols is that of equipment warm up time. The equipment and the solid CIPC act as a heat sink, which must be raised to operational temperatures for the aerosol generation process to function properly.

A fourth drawback to the creation of CIPC aerosols using a heated airstream is that the tubers themselves are subjected to heat stress as a consequence of being bathed in the heated aerosol or vapor. Heat stress reduces the storage life of the tubers and may also cause some discoloration of the product.

What is needed is a new tuber treatment process which does not require the conversion of solid CIPC to a liquid or to an aerosol or vapor, and which does not require the exposure of the stored tubers to heated air.

SUMMARY OF THE INVENTION

The present invention provides both a process and apparatus for treating tubers in storage with chlorpropham (CIPC) dust or the dust of any other similar organic compound. The process does not require the conversion of solid CIPC to a liquid, nor does it require the use of a heated airstream to vaporize or atomize the organic compound. The process includes the steps of forming minute particles of solid CIPC particles from a larger block or chunks of solid CIPC, and inducting the particles into an airstream which transports the particles to a tuber storage shed. The blocks or chunks of solid CIPC are fed into a hammer mill or like apparatus, which pulverizes the solid material. For a preferred embodiment of the process, each particle of the resulting powder has a major dimension of less than about 20 micrometers. The powder generated within the hammer mill is transported within a ducted airstream to a separator which returns, to the mill, particles having a major dimension of greater than about 5 micrometers for further pulverization. Fine powder consisting of particles, each of which has a major dimension of less than about 5 micrometers, is transported by the ducted airstream from the separator to a storage shed containing a pile of tubers. The particles of the CIPC dust are sufficiently fine that the powder filters through the pile and coats exposed surfaces of the exposed tubers. Sublimation of the CIPC dust particles results in a low vapor pressure of CIPC molecules within the storage shed. A state of equilibrium is soon achieved between solid and vapor states of the CIPC molecules within the shed. Thus, continuing sublimation and continuing recondensation of CIPC molecules ensure that all exposed surfaces of the tubers in the pile are soon covered by a film of CIPC.

For a preferred embodiment of the present invention, the airstream is created by a rotary screw air compressor. The compressed air is then chilled by passing it through a water-cooled heat exchanger. Any moisture that condenses in the heat exchanger is caught by a trap. From there, the air is passed through a venturi, which creates a low-pressure region in the airstream. The outlet port of the hammer mill is directed to this low-pressure region so that powder generated by the hammer mill is sucked into the airstream. For the preferred embodiment process, the airstream containing the powdered CIPC preferably enters the storage shed at a temperature of less than 18.33° C./65° F. This characteristic of the process is notable, as all other known methods for treating tubers with CIPC employ heated airstreams to deliver the CIPC to the tuber storage shed.

BRIEF DESCRIPTION OF THE DRAWINGS

FIG. 1 depicts the chemical structure of chlorpropham (CIPC);

FIG. 2 is an elevational view of the preferred embodiment apparatus for the treatment of tubers with CIPC dust, minus the air control system, shown coupled to a tuber storage facility;

FIG. 3 is a side elevational view of the separator;

FIG. 4 is a rear elevational view of the separator;

FIG. 5 is a front elevational view of the separator; and

FIG. 6 is a block diagram of the air control system used in combination with the preferred embodiment apparatus;

PREFERRED EMBODIMENT OF THE INVENTION

The present invention provides both a process and apparatus for treating tubers in storage with chlorpropham (CIPC) dust or the dust of any other similar organic compound that is a solid at ambient temperatures. The process does not require the conversion of solid CIPC to a liquid, nor does it require the use of a heated airstream to vaporize or atomize the organic compound. The process includes the steps of forming minute particles of solid CIPC particles from a block or chunks of solid CIPC, and inducting the particles into an airstream which transports the particles to a tuber storage shed. A distinguishing feature of the invention is that, for the preferred embodiment of the process, the airstream is maintained at or below ambient temperature.

The process and preferred apparatus used to implement the process will now be described with reference to the attached drawing figures. It should be understood that the drawings are not to scale, as they are intended to be merely descriptive of the process and apparatus.

Referring now to FIG. 2, an impact mill 201 is coupled to an internal combustion engine 202 via a toothed belt 203. The mill 201 and the engine 202 are mounted to a base 204. It should be obvious that other types of motors will serve equally well. Though not specifically shown, an electric motor, an air motor, a turbine or any other motor having the requisite power output may be substituted for the internal combustion engine 202. A guard 205 covers the belt 203. The mill 201 has a feed chute 206, into which solid CIPC 207 is fed. The mill 201 pulverizes the solid CIPC 207, which exits as a powder 208 through the outlet port 209. The powder 208, as it leaves the outlet port 209 is comprised of particles having a major dimension of generally less than 20 micrometers. An air jet 210, positioned within a first air duct 211, creates a an airstream that is pressurized above ambient pressure. Behind the air jet 210 is a region below ambient pressure. This partial vacuum, in combination with the airflow created by the mill 201, causes the powder 208 to enter the first air duct 211. The CIPC powder 208 is transported through a first duct 211 to a separator 212. The separator has a divider plate 213, which forces the airflow to reverse directions. Those particles which are generally larger than 5 micrometers are unable to successfully complete the direction reversal and fall to the bottom of the separator 212, from whence they are carried by return tube 215 back to the mill 201 for further pulverization. Fine power 216, comprised of particles having a major dimension of generally less than 5 micrometers, is transported by the airstream through a second duct 217 to a tuber storage facility 218 containing a pile of stacked tubers 219. The storage facility 218 has a vent 220 which communicates with the exterior via a filter 221. The particles of the fine CIPC powder 216 are sufficiently light that they filter through the stacked tubers 219 and coat exposed surfaces thereof. Sublimation of the particles of fine CIPC powder 216 results in a low vapor pressure of CIPC molecules within the storage facility 218. A state of equilibrium is soon achieved between solid and vapor states of the CIPC molecules within the storage facility 218. Thus, continuing sublimation and continuing recondensation of CIPC molecules ensure that all exposed surfaces of the tubers 219 in the pile are soon covered by a film of CIPC.

Referring now to FIGS. 3, 4 and 5, a preferred embodiment of the separator 212 is shown from three different angles. The numbers on the drawings correspond to the elements shown in FIG. 2.

Referring now to the air handling system of FIG. 6, a rotary screw compressor 601 provides a source of compressed air. Because compression of a gas increases its temperature, the stream of warm compressed air 602 expelled from the compressor 601 is passed through an heat exchanger, or aftercooler, 603. The aftercooler 603 is coupled to a chiller 604, which incorporates both a refrigeration unit 605 and a pump unit 606. Coolant is recirculated between the aftercooler 603 and the water chiller 604 by the pump unit 606. From the aftercooler 603, the cooled compressed air 607 is passed through a water trap 608, which removes any moisture 609, which may have condensed as it passed through the aftercooler 603. The dehumidified air 610 then passes through a low air pressure switch 611, which shuts down the mill 201 if air pressure drops below a set minimum. In order to maintain adequate airflow through the ducts 211, 215 and 217 (see FIG. 1), air pressure must be maintained within a range of about 5 to 10 lbs. per square inch. From the low air pressure switch 611, the compressed air is delivered to an air control solenoid valve 613. Air control solenoid valve 613 either turns on or shuts off air flow to the air jet 210. If the mill is shut down, air flow need be maintained only long enough to transport the CIPC powder 208 that has been pulverized by the mill 201 to the tuber storage facility 218. Conversely, air flow need be started only when the mill begins to pulverize CIPC. An air pressure regulator 614 maintains the air pressure delivered to the air jet 210 at a constant preset value indicated by gauge 615. Line 616 delivers compressed air to the air jet 210.

Although only single embodiments are described for both the method and the apparatus for treating tubers with CIPC dust it will be obvious to those having ordinary skill in the art that changes and modifications may be made thereto without departing from the scope and the spirit of the invention as hereinafter claimed.

What is claimed is:

1. A method for applying a sprout-inhibiting compound, that exists in a solid state at ambient temperatures, to tubers, the method comprising the steps of:
   providing a tuber storage enclosure in which are located tubers stacked, one on top of another;
   providing a compressor to generate a pressurized airstream;
   cooling the pressurized airstream by passing it through a heat exchanger;
   ducting the cooled pressurized airstream into the tuber storage enclosure;
   pulverizing solid sprout-inhibiting compound to generate a sprout-inhibiting powder;
   introducing the sprout-inhibiting powder into the cooled pressurized airstream, which transports it to the tuber storage enclosure and discharges it into the airspace surrounding the tubers, the discharged powder filtering through the stacked tubers.

2. The method of claim 1, wherein said sprout-inhibiting compound is chlorpropham.

3. The method of claim 1, wherein pulverization of the solid sprout-inhibiting compound is accomplished using an impact mill.

4. The method of claim 3, wherein the impact mill is a hammer mill.

5. The method of claim 1, wherein the airstream is provided by a screw-type compressor.

6. The method of claim 1, wherein a coolant circulates between a chiller, where its temperature is reduced, and the heat exchanger, where it absorbs heat from the airstream.

7. The method of claim 1, which further comprises the step of providing a venturi in order to create a region of pressure below ambient pressure, into which the pulverized to which the sprout inhibiting powder is introduced.

8. A method for applying the sprout-inhibiting compound, chlorpropham, to potatoes, the method comprising the steps of:
   placing the potatoes in a chamber;
   providing a compressor to generate a pressurized airstream;
   cooling the pressurized airstream by passing it through a heat exchanger;
   directing the cooled pressurized airstream into the chamber;
   pulverizing solid chlorpropham to generate chlorpropham powder;
   introducing the chlorpropham powder into the cooled pressurized airstream, which transports the chlorpropham powder into the chamber, the chlorpropham powder entering the chamber and coating the potatoes.

9. The method of claim 8, wherein pulverization of the solid chlorpropham is accomplished using an impact mill.

10. The method of claim 9, wherein the impact mill is a hammer mill.

11. The method of claim 8, wherein the airstream is provided by a screw-type compressor.

12. The method of claim 8, wherein a coolant circulates between a chiller, where its temperature is reduced, and the heat exchanger, where it absorbs heat from the airstream.

* * * * *